United States Patent [19]

Vrieland et al.

[11] Patent Number: 4,973,791
[45] Date of Patent: Nov. 27, 1990

[54] PROCESS OF OXIDIZING ALIPHATIC HYDROCARBONS EMPLOYING AN ALKALI-PROMOTED MOLYBDATE CATALYST

[75] Inventors: G. Edwin Vrieland; Craig B. Murchison, both of Midland, Mich.

[73] Assignee: The Dow Chemical Company, Midland, Mich.

[21] Appl. No.: 383,107

[22] Filed: Jul. 20, 1989

[51] Int. Cl.$^5$ .................. C07C 5/09; C07C 5/327; C07C 5/333; B01J 23/00

[52] U.S. Cl. .................. 585/624; 585/630; 585/631; 585/658; 585/663; 502/306

[58] Field of Search ............... 585/624, 630, 631, 658, 585/663; 502/306

[56] References Cited

U.S. PATENT DOCUMENTS

| | | | |
|---|---|---|---|
| 2,408,146 | 9/1946 | Kearby | 260/680 |
| 2,666,086 | 1/1954 | Pitzer | 260/680 |
| 3,119,111 | 1/1964 | McDonald et al. | 260/680 |
| 3,180,903 | 4/1965 | Lindquist et al. | 260/680 |
| 3,769,238 | 10/1973 | Tauster et al. | 502/306 |
| 3,862,256 | 1/1975 | Isailingold et al. | 260/680 E |
| 3,867,305 | 2/1975 | Flanigen et al. | 252/437 |
| 3,895,051 | 7/1975 | Umemura et al. | 260/465.3 |
| 4,144,197 | 3/1979 | Riesser | 252/462 |
| 4,152,300 | 5/1979 | Riesser | 252/462 |
| 4,172,854 | 10/1979 | Ellis et al. | 585/445 |
| 4,220,560 | 9/1980 | Anquetil et al. | 252/468 |
| 4,229,604 | 10/1980 | Tmenov et al. | 585/445 |
| 4,250,346 | 2/1981 | Young et al. | 585/658 |
| 4,309,361 | 1/1982 | Suresh et al. | 260/465.3 |
| 4,336,409 | 6/1982 | Yamamoto et al. | 585/622 |
| 4,388,223 | 6/1983 | Ferlazzo et al. | 252/437 |
| 4,532,083 | 7/1985 | Suresh et al. | 260/465.3 |
| 4,596,787 | 6/1986 | Manyik et al. | 502/312 |
| 4,629,719 | 12/1986 | Kukes et al. | 502/306 |
| 4,711,930 | 12/1987 | Hoelderich et al. | 502/209 |
| 4,746,753 | 5/1988 | Brazdil, Jr. et al. | 558/324 |

FOREIGN PATENT DOCUMENTS 0471781 7/1978 U.S.S.R. .................. 585/630

OTHER PUBLICATIONS

V. P. Luk'yanenko et al., Zhurnal Prikladnoi Khimi, Nr. 5, 1987, pp. 1168–1171.
L. P. Shapovalova et al., Zh. Prikl. Khim. (Leningrad), vol. 60(2), 1987, 369–373.
M. A. Chaar et al., Journal of Catalysis 105, 483–498, (1987).
L. P. Shapovalova et al., Kata. Katal. 23, (1985), 87–90.
G. A. Vorob'eva et al., Journal of Catalysis 71, 405–410, (1981).
D. N. Tmenov et al., Russian Journal of Physical Chemistry, 51, (7), 1027–1028, (1977).
Chemical Abstracts 100:104860q, (1984).
Chemical Abstracts 74:114055e, (1971).
Derwent 91463R-AE, (1970).
Derwent 06949C/04, (1980).

*Primary Examiner*—Helen M. S. Sneed
*Assistant Examiner*—J. Saba

[57] ABSTRACT

A process for the production of unsaturated aliphatic hydrocarbons, such as diolefins, comprising contacting an aliphatic hydrocarbon, such as an alkane or a monoolefin, with a solid heterogeneous catalyst containing labile oxygen under reaction conditions such that a more highly unsaturated aliphatic hydrocarbon is selectively formed in a high space-time yield. The catalyst comprises an oxide of magnesium, an oxide of molybdenum, an alkali metal promoter, and optionally an oxide of vanadium. For example, butane is oxidized in the presence of magnesium molybdate doped with alkali metal-oxide to a mixture of products including predominantly butadiene and cis-2-butene and trans-2-butene.

34 Claims, No Drawings

PROCESS OF OXIDIZING ALIPHATIC HYDROCARBONS EMPLOYING AN ALKALI-PROMOTED MOLYBDATE CATALYST

BACKGROUND OF THE INVENTION

This invention pertains to a process for the oxidation of aliphatic hydrocarbons, such as alkanes and monoolefins, to products comprising more highly unsaturated aliphatic hydrocarbons. More specifically, this invention pertains to the oxidation of butane to butadiene.

Unsaturated aliphatic hydrocarbons, such as monoolefins and diolefins, are useful as monomers and comonomers in the preparation of polyolefin plastics.

U.S. Pat. No. 3,180,903 discloses a process for the dehydrogenation of aliphatic hydrocarbons containing from two to five carbon atoms. Butanes, for example, can be converted to butenes and butadienes. The catalyst used in this process is taught to contain chromium oxides or molybdenum oxides supported on a gel-type alumina. Optionally, the catalyst may contain one or more alkali metal oxides. Disadvantageously this process is limited to a low hydrocarbon conversion and a low ultimate yield of butadiene.

U.S. Pat. No. 3,119,111 discloses a process for the oxidative dehydrogenation of a $C_4$ to $C_6$ alkane having a four carbon chain to a 1,3-alkadiene. The reaction occurs in the presence of oxygen and a catalyst containing an alkali metal molybdate, such as lithium molybdate. Disadvantageously, this process requires potentially explosive mixtures of alkanes and oxygen.

U.S. Pat. No. 3,862,256 discloses a process for the oxidative dehydrogenation of paraffin hydrocarbons, such as butane, over a catalyst containing oxy compounds of molybdenum and magnesium, and optionally, vanadium. When butane is contacted with the catalyst, the products include butenes and butadiene: however, the selectivity and space-time yield of butadiene is lower than desired.

U.S. Pat. No. 4,229,604 discloses a process for the oxidative dehydrogenation of a paraffin, such as butane, to unsaturated hydrocarbons, such as butenes and butadiene. The catalyst is an oxide of molybdenum deposited on a carrier. The carrier is selected from the group consisting of granulated porous crystalline silica modified with magnesia, magnesium-titanium oxides, or magnesium-aluminum oxides. It is taught that the silica carrier is prepared from an an alkali metal silicate. It is further taught that on the surface of the catalyst there exists an active magnesium molybdate. Disadvantageously, the catalyst of this process produces a selectivity and space-time yield of butadiene which is too low for industrial use.

While the oxidation of aliphatic hydrocarbons is well researched in the prior art, the selectivity and productivity to particular unsaturated hydrocarbons, such as diolefins, fall short of those which are desired for commercial exploitation. Accordingly, it would be desirable to have a selective, direct oxidation of an aliphatic hydrocarbon, such as an alkane or monoolefin, to the corresponding unsaturated aliphatic hydrocarbons, specifically the diolefin. It would be more desirable if the alkane is butane and the diolefin is butadiene. It would be most desirable if such an oxidation produced a high selectivity and space-time yield of the diolefin and other olefins, and correspondingly low selectivities to deep oxidation products, such as carbon dioxide.

SUMMARY OF THE INVENTION

In one aspect, this invention is a process of preparing an unsaturated aliphatic hydrocarbon comprising contacting an aliphatic hydrocarbon having at least three carbon atoms with a catalyst of this invention, described hereinafter. Under the reaction conditions of the process of this invention unsaturated aliphatic hydrocarbons, such as diolefins, are formed in a selectivity of at least about 50 mole percent.

In another aspect, this invention is a solid heterogeneous catalyst composition containing labile oxygen, said catalyst being capable of being employed in the above-identified process of preparing unsaturated aliphatic hydrocarbons. The catalyst consists essentially of an oxide of magnesium, an oxide of molybdenum, and an alkali metal promoter in a concentration from about 0.1 weight percent to about 5 weight percent calculated as alkali hydroxide and based on the weight of the combined magnesium and molybdenum oxides. Optionally, the catalyst can contain an oxide of vanadium.

Advantageously, aliphatic hydrocarbons can be oxidized directly and selectively to more highly unsaturated aliphatic hydrocarbons by the process of this invention. Surprisingly, the process of this invention produces a high selectivity and space-time yield of more highly unsaturated aliphatic hydrocarbons, especially diolefins. More surprisingly, the process of this invention produces low selectivities and yields of undesirable deep oxidation products, such as carbon monoxide and carbon dioxide. Unexpectedly, butadiene can be produced directly from butane in high selectivity and space-time yield by the process of this invention while maintaining low selectivities of deep oxidation products. For the purposes of this invention, the "space-time yield" is defined as the numerical product of the space velocity, the conversion, the selectivity, and the concentration of the aliphatic hydrocarbon in the feedstream, the preceding terms being defined hereinafter.

Unsaturated aliphatic hydrocarbons, such as monoolefins and diolefins are useful as monomers or comonomers in the formation of polyolefins. Butadiene is also potentially useful as an intermediate in the preparation of styrene.

DETAILED DESCRIPTION OF THE INVENTION

The aliphatic hydrocarbons which can be employed in the process of this invention include alkanes and olefins which have three or more carbon atoms.

The alkanes can be alternatively described as paraffin hydrocarbons. These compounds are known to those skilled in the art as saturated hydrocarbons. As noted hereinbefore, the alkanes contain at least three carbon atoms, and additionally, can have straight-chain, branched or cyclic structures. Typically, the alkane contains up to about 20 carbon atoms. Examples of suitable alkanes include n-butane, n-pentane, n-hexane, n-heptane, n-octane, n-nonane, n-decane, n-dodecane, and higher saturated homologues, as well as isobutane, isopentane, neopentane, and likewise branched hexanes, heptanes, octanes, nonanes, decanes, dodecanes, and higher branched homologues. Cyclobutane, cyclopentane, cyclohexane, cycloheptane, cyclooctane, methylcyclopentane, methylcyclohexane and other alkyl-substituted cycloalkanes are also suitable. Preferably, the alkane is normal or linear.

The olefins can be further described as aliphatic hydrocarbons containing at least one unsaturated double bond. As noted earlier, the olefins should also contain at least 3 carbon atoms, and typically up to about 20 carbon atoms. The location of the double bond is not critical; therefore, the double bond can occur at a terminal or internal location along the carbon chain. Preferably, however, the olefin has a normal or linear structure, rather than a branched structure. For example, 1-butene is preferred over isobutylene. Thus, some examples of suitable olefins include, 1-butene, 2-butene, 1-pentene, 2-pentene, 3-pentene, 1-hexene, 2-hexene, 3-hexene, and likewise 1-heptene, 1-octene, 1-nonene, 1-decene, and isomers thereof wherein the unsaturation occurs at any other position along the carbon chain. Vinylcyclohexane is also suitably employed. Olefins containing more than one double bond, such as 1,3-hexadiene and isoprene, are also acceptable, being converted in the process of this invention to more highly unsaturated hydrocarbons. Cyclic olefins, such as cyclohexene and vinylcyclohexane, are also suitable starting materials. Preferably, the olefin is a monoolefin. More preferably, the olefin is 1- or 2-butene.

The many examples of aliphatic hydrocarbons, noted hereinabove, are representative of those which are suitable for the process of this invention, and are not intended to be limiting thereof. Other aliphatic hydrocarbons may be available to one skilled in the art and may also be suitable for the process of the invention.

The preferred alkanes are normal paraffins which can be represented by the general formula:

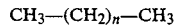

$$CH_3-(CH_2)_n-CH_3$$

wherein n is an integer from 1 to 8. More preferably, n is an integer from 2 to 6. Most preferably, n is 2, and the alkane is n-butane.

Optionally, the aliphatic hydrocarbon reactant can be diluted with a non-reactive gas, such as nitrogen, helium, argon, methane, carbon dioxide or steam. While the type of diluent is determined by prevailing economic considerations, a preferable diluent is nitrogen. If a diluent is used, the amount can vary depending upon the design of the reactor and the capacity of the solid oxidant. Preferably, the hydrocarbon content of the hydrocarbon/diluent mixture is not greater than about 95 mole percent. More preferably, the hydrocarbon content of the mixture ranges from about 10 mole percent to about 90 mole percent. Most preferably, the hydrocarbon content of the mixture ranges from about 40 mole percent to about 90 mole percent.

The catalyst of this invention, described in detail hereinbelow, is a solid heterogeneous oxide, at least a portion of the oxygen of which is labile. By this it is meant that a free form of oxygen is present in the catalyst, and that this free form of oxygen is capable of oxidizing the aliphatic hydrocarbon. Thus, in one aspect the catalyst of this invention is a solid oxidant. After the labile oxygen is removed through reaction, the catalyst is spent. Moreover, the catalyst may build up over time a carbonaceous residue on its surface. The spent and poisoned catalyst can be regenerated by contact with a source of gaseous oxygen. Thus, in addition to the aliphatic hydrocarbon, oxygen is required for the catalytic process of this invention.

Oxygen is typically supplied from a gaseous source provided as a continuous oxygen-containing feed. Any source of oxygen is acceptable, such as pure gaseous elemental oxygen, air, or nitrous oxide. The preferred source of oxygen is gaseous air. Optionally, the gaseous elemental oxygen can be diluted with a non-reactive gas, such as nitrogen, helium, argon, or carbon dioxide. Preferably, the diluent is nitrogen. If a non-reactive diluent is employed, the oxygen content of the mixture is preferably not greater than about 50 mole percent. More preferably, the oxygen content of the mixture ranges from about 0.5 mole percent to about 30 mole percent. Most preferably, the oxygen content of the mixture ranges from about 1 mole percent to about 20 mole percent.

The amount of oxygen employed in the catalytic process of this invention is any amount which is (1) sufficient to oxidize fully the solid heterogeneous catalyst, and (2) sufficient to remove carbonaceous residues from the catalyst's surface. Preferably, the regeneration of the catalyst is carried out separately from the oxidation of the aliphatic hydrocarbon.

Alternatively, it is acceptable to co-feed a small amount of gaseous elemental oxygen with the aliphatic hydrocarbon. The function of the co-feed is to burn off carbonaceous residues on the surface of the catalyst, and to replenish to some extent the labile oxygen. The concentration of oxygen in the aliphatic hydrocarbon and oxygen feed is limited by the explosive limits of this mixture. Preferably, the oxygen concentration is maintained below the lower explosive limit. For example, if the aliphatic hydrocarbon is butane, the oxygen concentration is preferably no greater than about 10 mole percent, more preferably, no greater than about 8 mole percent.

The solid heterogeneous catalyst employed in the process of this invention consists essentially of an oxide of magnesium, an oxide of molybdenum, and an alkali metal promoter. Any source of magnesium oxide is acceptable: however, MgO is preferred. Likewise, any source of molybdenum oxide is acceptable, including for example, $MoO_3$, $(NH_4)_6Mo_7O_{24}\cdot 4H_2O$, and $(NH_4)_2MoO_4$. The molybdenum oxide can also be obtained from a precursor molybdenum compound, such as molybdenum carbonyls like $Mo(CO)_6$. Preferably, the source of molybdenum oxide is $(NH_4)_6Mo_7O_{24}\cdot 4H_2O$. The alkali metal promoter is a Group IA metal compound possessing a basicity sufficient to increase the formation of higher unsaturates in the process of this invention. Small amounts of other elements may be present in the catalyst, provided that these elements do not materially change the performance of the catalyst.

The catalyst containing the mixed magnesium-molybdenum oxides and alkali metal promoter can be simply prepared. Generally, the desired quantity of a molybdenum oxide or precursor compound, such as ammonium heptamolybdate or molybdenum carbonyl, is dissolved in a solvent to make a solution. Preferably, the molybdenum compound is ammonium heptamolybdate, and the solvent is water. The solution is poured over magnesium oxide to form a slurry, which is thereafter dried to remove solvent. If the solution is aqueous, the drying is conducted in an oven at a temperature in the range from about 70° C. to about 120° C. The dried composition is calcined to form a catalytically active magnesium oxide-molybdenum oxide mixture. The calcination is typically conducted at a temperature ranging from about 550° C. to about 650° C. for a time ranging from 1 hour to about 24 hours. Preferably, the calcination is conducted at about 600° C. for at least about 2 hours. Alternatively, the dried composition, described hereinabove, can be employed directly with no prior calcination in the catalytic process of this invention. Since the molybdenum compound can be converted into molybdenum oxide at or about 300° C., and since the catalyst bed is heated to a temperature higher than about 300° C., the dried composition will be converted in situ into a catalytically active magnesium oxide-molybdenum oxide mixture.

The mixed oxide catalyst composition may appear amorphous by X-ray diffraction, or may contain diffraction peaks characteristic of magnesium molybdate. The elemental analysis of the calcined solid reveals a composition ranging from about 6 weight percent $MoO_3$ to about 50 weight percent $MoO_3$ and from about 94 weight percent MgO to about 50 weight percent MgO. Preferably, the composition ranges from about 10 weight percent $MoO_3$ to about 30 weight percent $MoO_3$ and from about 90 weight percent MgO to about 70 weight percent MgO; more preferably, from about 15 weight percent $MoO_3$ to about 25 weight percent $MoO_3$ and from about 85 weight percent MgO to about 75 weight percent MgO.

It is required to add to the mixed oxide catalyst, described hereinbefore, at least one alkali metal promoter. The promoter serves to increase the selectivity and space-time yield of unsaturated products, e.g. diolefins, in the process of this invention. Such a promoter is typically a compound of lithium, sodium, potassium, rubidium, cesium or francium of sufficient basicity to improve the selectivity to higher unsaturates in the process of this invention. Suitable compounds include the alkali oxides, hydroxides and carbonates. Compounds which decompose on heating to the oxides are also suitable, such as alkali metal acetates and oxalates. Alkali metal salts may be found which are also suitable, although typically, the alkali metal halides and alkali metal silicates are not preferred due to their lower basicity. Preferably, the alkali metal promoter is an alkali metal oxide, hydroxide, carbonate, acetate, or oxalate. More preferably, the alkali metal promoter is an oxide or hydroxide of potassium or cesium. Most preferably, the alkali metal promoter is an oxide or hydroxide of potassium.

The amount of alkali metal promoter is critical to the performance of the catalyst. Generally, any amount of alkali metal promoter is acceptable which is sufficient to increase the selectivity and the space-time yield of unsaturated products, such as diolefins, in the process of this invention. Typically, the amount of alkali metal promoter calculated as the alkali hydroxide is in the range from about 0.1 weight percent to about 5 weight percent based on the total weight of the magnesium and molybdenum oxides. Preferably, the amount of alkali metal promoter calculated as the alkali metal hydroxide is in the range from about 0.2 weight percent to about 2 weight percent based on the weight of the magnesium-molybdenum oxides, more preferably, in the range from about 0.5 weight percent to about 1.5 weight percent. Below the lower preferred amount of alkali metal promoter the selectivity to diolefin is reduced while the selectivity to deep oxidation products is increased. Above the upper preferred amount of alkali metal promoter the selectivity to diolefin is also reduced.

The alkali metal promoter can be added to the molybdate catalyst in a variety of ways known to those in the art. For example, the promoter can be applied by the well-known impregnation technique, described for example by Charles N. Satterfield in *Heterogeneous Catalysis in Practice*, McGraw-Hill Book Company, New York, 1980, pp. 82–83, incorporated herein by reference. In this technique the magnesium-molybdenum oxide mixture is immersed in a solution of the alkali metal promoter, for example, a methanolic solution of the alkali metal oxide or hydroxide. The alkali-impregnated magnesium molybdate is then drained of excess solution, dried in an oven to remove residual solvent, and calcined at a temperature in the range from about 550° C. to about 650° C. to bind the alkali metal promoter to the molybdate.

Optionally, the molybdate catalyst of this invention can contain an activator which functions to increase the activity of the catalyst at any given temperature. Preferably, the activator does not decrease significantly the selectivity to diolefins and monoolefins. Preferably, the activator allows the reaction to be run at a lower temperature, while achieving high selectivity and high space-time yields of diolefins. Activators which are suitable for incorporation into the catalyst include the oxides of vanadium. Preferably, the activator is $V_2O_5$. Any amount of vanadium oxide can be added to the catalyst provided that (1) the activity of the catalyst is increased, and (2) the selectivity for alkenes, including mono- and diolefins, is not significantly decreased. Generally, if an activator is used, the concentration ranges from about 0.05 weight percent to about 30 weight percent based on the total weight of the catalyst. Preferably, the concentration of activator ranges from about 1 weight percent to about 10 weight percent based on the total weight of the catalyst, more preferably, from about 1 weight percent to about 3 weight percent based on the total weight of the catalyst. The activator can be incorporated into the magnesium oxide and molybdenum oxide slurry prior to calcination, or can be applied to the calcined magnesium-molybdenum oxides by the impregnation technique, described hereinbefore.

Optionally, the molybdate catalyst can be applied to an inert support. Suitable supports include non-acidic alumina, silica, titania, and $MgAl_2O_4$.

The process of this invention can be carried out in any suitable reactor, including batch reactors, continuous fixed-bed reactors, slurry reactors, fluidized bed reactors, and riser reactors. Preferably, the reactor is a continuous flow reactor, such as a continuous fixed-bed reactor or a riser reactor of the type described hereinafter.

Typically, the riser reactor comprises an upright vessel of relatively low ratio of diameter to length. The catalyst is continuously charged into the bottom of the riser reactor. Likewise, the aliphatic hydrocarbon feedstream is delivered concurrently to the bottom of the riser reactor as a vapor phase feed or as a liquid phase feed. Preferably, the alkane is delivered as a vapor phase feed pre-mixed with an inert, gaseous diluent, and optionally, a small concentration of oxygen. The feed moves upward through the reactor, thereby contacting the catalyst. Upon contacting the catalyst, the feed is converted into a mixture of products, including monoolefins, diolefins, higher unsaturated olefins, cracking products, deep oxidation products, such as carbon monoxide and carbon dioxide, and heavies, such as benzene and furan in the case of a butane feed. The product stream exits the riser reactor and is separated by known methods, such as distillation, to recover the desired products, typically the diolefins. Unreacted alkanes and monoolefin products are recycled to the riser reactor for further oxidation.

Riser reactor technology is advantageous for the process of this invention, because (1) the hazard of using a feedstream containing a mixture of alkane and/or olefin and elemental oxygen is eliminated, and (2) the selectivity for diolefins is enhanced, especially at the high temperatures required for this process. In contrast, if a feedstream of alkane and oxygen is employed at a high temperature and a high oxygen/alkane mole ratio, there is a tendency to produce more deep oxidation products, such as carbon monoxide and carbon dioxide. In addition, the danger of a run-away reaction is greater.

The operation of a riser reactor can be simulated by employing a method of alternating pulses. Thus, a pulse of the hydrocarbon-containing feed is passed through the catalyst bed where it is oxidized to form the desired olefin products. Next, a pulse of inert gas is passed through the catalyst bed to purge the bed of residual alkanes and alkenes. After purging, a pulse of oxygen-containing feed is passed through the catalyst bed to regenerate the catalyst. Finally, a second pulse of inert gas is passed through the catalyst bed to purge the bed of oxygen, after which the cycle is repeated. Such a procedure is employed in the illustrative embodiments, described hereinafter.

The aliphatic hydrocarbon reactant is contacted with the catalyst at any operable temperature which promotes the oxidation process of this invention and yields the desired unsaturated products. Typically, the temperature is in the range from about 400° C. to about 700° C. Preferably, the temperature is in the range from about 500° C. to about 650° C. More preferably, the temperature is in the range from about 530° C. to about 600° C. Below the preferred lower temperature the conversion of reactant may be low. Above the preferred upper temperature the selectivity and yield of diolefin products may decrease.

Likewise, the aliphatic hydrocarbon reactant is contacted with the catalyst at any operable pressure which promotes the oxidation process of this invention and yields the desired unsaturated products. Typically, the partial pressure of the reactant is adjusted to maintain the reactant in the vapor state at the operating temperature. Preferably, the partial pressure of the aliphatic hydrocarbon is in the range from about subatmospheric to about 100 psia. More preferably, the partial pressure is in the range from about 1.5 psia to about 30 psia. Most preferably, the partial pressure is in the range from about 3 psia to about 15 psia.

When the process of this invention is conducted in a continuous flow reactor, described hereinbefore, the flow rate of the reactants can be varied. Generally, in the process of this invention the aliphatic hydrocarbon reactant is fed into the reactor at any operable flow rate which promotes the oxidation reaction and yields the desired unsaturated products. The flow rate is expressed as the gas hourly space velocity (GHSV) and is given in units of volume of aliphatic hydrocarbon-containing gaseous feed per total reactor volume per hour or simply $hr^{-1}$. It is preferred to employ a gas hourly space velocity in the range from about 100 $hr^{-1}$ to about 10,000 $hr^{-1}$, more preferably in the range from about 400 $hr^{-1}$ to about 4000 $hr^{-1}$; most preferably, in the range from about 1000 $hr^{-1}$ to about 2000 $hr^{-1}$. It should be understood that the space velocity controls the residence time of the reactants.

For the case of the riser reactor, after contacting the catalyst with the aliphatic hydrocarbon reactant the spent catalyst leaves the top of the reactor and is transported into a second reactor for regeneration. Regeneration is effected by contact with oxygen. Typically, a preheated oxygen source, like that described hereinbefore, is fed into the bottom of the second reactor. The spent catalyst is contacted with the oxygen source at any operable temperature, pressure, and oxygen-source flow rate which are sufficient to regenerate the catalyst. The process variables should be controlled, however, so as to prevent a runaway reaction or the buildup of excessive heat. Preferably, the temperature is in the range from about 500° C. to about 700° C., more preferably, in the range from about 550° C. to about 650° C. Preferably, the pressure is in the range from subatmospheric to about 50 psig, more preferably, in the range from about 15 psig to about 30 psig. The oxygen-source flow rate required will depend upon the heat transfer properties of the particular reactor. For example, at some high flow rates the temperature may rise dramatically resulting in an uncontrolled reaction.

When the aliphatic hydrocarbon is contacted with the catalyst of this invention, an oxidation of the aliphatic hydrocarbon occurs resulting in the loss of at least two hydrogen atoms from the hydrocarbon reactant with formation of by-product water. The organic products which are produced are predominantly unsaturated aliphatic hydrocarbons, such as monoolefins and diolefins. These unsaturated products usually contain the same number of carbon atoms as the reactant aliphatic hydrocarbon. Thus, these products are not products of cracking, which would contain fewer carbon atoms than the starting hydrocarbon. Generally, also the unsaturated products possess a higher degree of unsaturation than the reactant hydrocarbon. For example, alkanes, such as butane, can lose two hydrogen atoms to yield monoolefins, such as 1-butene, trans-2-butene, and cis-2-butene. In turn, monoolefins, such as the butenes previously cited, can lose two hydrogen atoms to form 1,3-butadiene.

The preferred diolefin products can be represented by the general formula:

$$CH_2=CH-CH=CH-(CH_2)_m-H$$

wherein m is an integer from 0 to about 6. Preferably, m is an integer from 0 to about 2. More preferably, m is 0 and the unsaturated product is 1,3-butadiene. Isomers of the formula shown hereinabove can also be formed wherein the unsaturation occurs at any other location along the carbon chain. Preferably, the unsaturation occurs in a conjugated fashion, as exemplified in the product 1,3-butadiene. Even more unsaturated variants of the general formula can be formed wherein further oxidation has occurred to yield more than two ethylenic double bonds. Alkynes, however, are not formed in significant amounts.

In addition to alkenes, the product stream can contain by-products of various types. For example, when the saturated alkane is n-butane, small quantities of cracking products, such as propylene and ethylene, can be formed, as well as heavies, such as benzene and furan, and deep oxidation products, such as carbon monoxide and carbon dioxide. Unexpectedly, however, these by-products, especially the deep oxidation products, are significantly reduced over the prior art processes.

For the purposes of this invention, "conversion" is defined as the mole percentage of aliphatic hydrocarbon reactant lost from the feed stream as a result of reaction. The conversion can vary widely depending upon the reactants, the form of the catalyst, and the process conditions such as temperature, pressure, flow rate, and catalyst residence time. Within the preferred temperature range, as the temperature increases the conversion generally increases. Within the preferred gas hourly space velocity range, as the space velocity increases the conversion generally decreases. Typically, the conversion of the aliphatic hydrocarbon is at least about 10 mole percent. Preferably, the conversion is at least about 20 mole percent; more preferably, at least about 30 mole percent; even more preferably, at least about 40 mole percent; and most preferably, at least about 50 mole percent.

Likewise, for the purposes of this invention "selectivity" is defined as the mole percentage of converted carbon which forms a particular product. Typically, selectivities also vary widely depending upon the reactants, the form of the catalyst, and the process conditions. Typically, the process of this invention achieves high selectivities to diolefins. Within the preferred temperature range, as the temperature increases the selectivity for alkenes generally decreases. Within the preferred space velocity range, as the space velocity increases the selectivity for alkenes generally increases. Preferably, the combined selectivity to all alkenes is at least about 50 mole percent; more preferably, at least about 60 mole percent even more preferably, at least about 70 mole percent; most preferably, at least about 80 mole percent. Typically, the selectivity to diolefins is at least about 40 mole percent. Preferably, the selectivity to diolefins is at least about 50 mole percent, more preferably, at least about 60 mole percent, most preferably, at least about 70 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 0.65, or 65 mole percent, and a selectivity to diolefin of 0.75, or 75 mole percent, would have a diolefin yield of 0.49, or 49 mole percent. Typically, the yield of diolefin achieved in the process of this invention is at least about 8 mole percent. Preferably, the yield of diolefin achieved in the process of this invention is at least about 18 mole percent, more preferably at least about 28 mole percent, most preferably, at least about 35 mole percent. Typically, in the oxidation of butane the yield of total $C_4$ olefins is at least about 25 mole percent. Preferably, in the oxidation of butane the yield of total $C_4$ olefins is at least about 30 mole percent, more preferably, at least about 35 mole percent, most preferably, at least about 40 mole percent.

The rate at which a desired product is produced in the process of this invention can be expressed in the concept of space-time yield. The "space-time yield" is defined as the mole percentage yield of a given product per hour (yield $hr^{-1}$), and it is the numerical product of the single-pass conversion, the selectivity, the gas hourly space velocity, and the concentration of the aliphatic hydrocarbon in the feedstream. Preferably, the space-time yield of diolefin in the process of this invention is at least about 30 mole percent per hour, more preferably, at least about 120 mole percent per hour, and most preferably, at least about 200 mole percent per hour.

ILLUSTRATIVE EMBODIMENTS

The following examples are illustrative of the process and catalyst of this invention, but are not intended to be limiting thereof. All percentages are given in mole percent carbon, unless noted otherwise.

EXAMPLES 1-5

(a) Preparation of Cesium-Promoted Catalysts 1-5

A series of cesium-doped, molybdate catalysts is prepared according to the following general procedure with the exception that the quantity in grams of cesium hydroxide monohydrate per 40 g methanolic solution is varied as follows: Catalyst 1, 0.16 g; Catalyst 2, 0.23 g; Catalyst 3, 0.29 g; Catalyst 4, 0.53 g; and Catalyst 5, 0.76 g.

Ammonium heptamolybdate, $(NH_4)_6Mo_7O_{24}\cdot 4H_2O$ (72 g; 0.0583 moles), is dissolved in 175 ml of water. The resulting solution is mixed with magnesium hydroxide (300 g; Alfa Research Chemicals & Materials) to form a slurry. The slurry is dried at 70° C. for 18 hours and at 130° C. for 2 hours to obtain a solid mixture. The solid is crushed and passed through a sieve to obtain particles having a 20-120 mesh size. The sieved particles are calcined by heating slowly over 5 hours to a temperature of 600° C. and then holding at 600° C. for 2 hours. The calcined solid is cooled to room temperature to yield magnesium molybdate comprising 22 weight percent $MoO_3$ and 78 weight percent MgO. A methanolic solution is prepared by adding the appropriate weight of cesium hydroxide, $CsOH\cdot H_2O$, as cited hereinabove, to methanol to give 40 g of methanolic solution. The magnesium molybdate (20.6 g) is immersed for 15 minutes in 40 g of methanolic solution. The resulting mixture is filtered, and the filtered solid is dried in air at room temperature (taken as about 22° C.) for 4 hours and then in a drying oven at 120° C. for 16 hours. The dried solid is calcined by heating over 5 hours to a temperature of 600° C., and then by holding for 2 hours at 600° C. to yield a cesium-promoted magnesium molybdate catalyst. The weight percentage of cesium in Catalysts 1-5 is set forth in Table I.

TABLE I*

| Example | 1 | 2 | 3 | 4 | 5 |
| --- | --- | --- | --- | --- | --- |
| Catalyst: | 1 | 2 | 3 | 4 | 5 |
| Weight % Cs | 0.55 | 0.90 | 0.87 | 1.88 | 2.92 |
| Surface Area ($m^2/g$) | 100.0 | 94.2 | 81.9 | 86.6 | 72.8 |
| % Conversion | 61.87 | 47.70 | 44.75 | 29.91 | 19.28 |
| % Selectivities: | | | | | |
| 1-butene | 2.26 | 4.92 | 5.61 | 10.34 | 13.65 |
| tr-2-butene | 1.29 | 1.88 | 2.37 | 2.96 | 4.40 |
| cis-2-butene | 1.59 | 2.82 | 2.64 | 4.54 | 6.60 |
| butadiene | 71.30 | 71.09 | 73.85 | 53.37 | 38.49 |
| % Total C4's | 76.44 | 80.71 | 84.46 | 71.21 | 63.13 |
| propylene | 0.33 | 0.50 | 0.33 | 3.14 | 7.80 |
| ethylene | 2.56 | 3.23 | 3.36 | 5.83 | 8.70 |
| % Total Cracking | 2.89 | 3.73 | 3.69 | 8.98 | 16.49 |
| $CO_2$ | 9.89 | 4.78 | 4.70 | 4.22 | 7.41 |
| CO | 4.17 | 1.78 | 2.51 | 2.69 | 5.30 |
| % Deep Oxidation | 14.06 | 6.56 | 7.21 | 6.91 | 12.71 |
| Furan/Benzene | 4.80 | 3.28 | 1.63 | 2.65 | 1.30 |
| Unknown | 1.82 | 5.72 | 3.00 | 10.25 | 6.37 |
| % Total Heavies | 6.61 | 9.00 | 4.64 | 12.90 | 7.67 |
| % Yield C4's | 47.29 | 38.50 | 37.80 | 21.30 | 12.17 |
| Total C balance | 98.88 | 97.72 | 98.66 | 96.93 | 98.77 |

*Catalyst, 15 cc; T = 550° C.; GHSV = 336 $hr^{-1}$.

(b) Oxidation of Butane Employing Catalysts 1-5

Catalysts 1-5, prepared hereinabove, are tested in the oxidation of butane according to the following general procedure: The catalyst (15 cc) is loaded into a Vycor glass tube reactor (7.6 cm length × 18 mm O.D.). The Vycor glass tube is connected at the top to an inlet tube for the feed stream, and at the bottom to an outlet tube for collection of the products. The temperature of the reactor, as measured from a ⅛ inch O.D. stainless steel thermowell embedded in the catalyst bed, is raised to 550° C. A feedstream containing 10 volume percent butane, 50 volume percent nitrogen, and 40 volume percent helium is passed through the catalyst bed at a rate of 84 ml/min (GHSV=336 hr$^{-1}$) for 30 seconds. The feed stream is halted, and a purge stream containing helium is passed through the catalyst bed at a rate of 84 ml/min for 1 minute. The purge stream is halted, and an oxygen stream containing 10 volume percent oxygen in helium is passed through the catalyst bed at a similar flowrate for 1 minute. The oxygen stream is halted, and a final purge stream of helium is passed through the catalyst bed at a similar flowrate for 1 minute. The complete cycle is repeated for a total of 30 minutes, and the combined products are collected in a Saran ® polyvinylidene chloride plastic bag. The products are analyzed by gas phase chromatography using a Carle multi-column Gas Chromatograph fitted with the following ⅛" diameter columns: (1) 2.70 percent Carbowax 1540 on Porasil C (21", 80/100 mesh, T$_{max}$ 175° C.); (2) 3.0 percent Carbowax 1540 on Porasil C (4', 60/80 mesh, T$_{max}$ 150° C.); (3) 27.5 percent BIS 2(XE)A on Chromosorb PAW (17', 45/60 mesh, T$_{max}$ 150° C.); (4) Porapak Q (9', 50/80 mesh, T$_{max}$ 250° C.); (5) Molecular Sieve 13X (9', 45/60 mesh, T$_{max}$ 300° C.); (6) Molecular Sieve 5A (3', 80/100 mesh, T$_{max}$ 300° C.); and (7) 28 percent DC 200/500 on Chromosorb PAW (3.5', 60/80 mesh, T$_{max}$ 175° C.). The process results are set forth in Table I. The data show that butane is oxidized predominantly to butadiene and butenes in the presence of the magnesium molybdate catalyst doped with cesium.

COMPARATIVE EXPERIMENT 1

A composition is prepared in the manner described for Catalysts 1-5 hereinbefore, except that the steps pertaining to the doping of cesium are eliminated. The resulting composition contains 22 weight percent MoO$_3$ and 78 weight percent MgO. There is no cesium in the composition. The composition is employed as a catalyst in the oxidation of butane in the manner described in Examples 1-5 (b) with the results given in Table II.

TABLE II*

| Comparative Experiment 1 | GHSV 336/hr | GHSV 600/hr |
|---|---|---|
| Weight % Cs | 0.0 | 0.0 |
| Surface Area (m²/g) | 107.9 | 107.9 |
| % Conversion | 67.78 | 52.78 |
| % Selectivities: | | |
| 1-butene | 1.43 | 2.55 |
| trans-2-butene | 1.40 | 2.33 |
| cis-2-butene | 1.15 | 2.17 |
| butadiene | 46.55 | 58.50 |
| % Total C4's | 50.53 | 65.55 |
| propylene | 0.78 | 0.74 |
| ethylene | 2.14 | 1.74 |
| % Total Cracking | 2.93 | 2.48 |
| CO$_2$ | 27.18 | 16.17 |
| CO | 10.28 | 6.41 |

TABLE II*-continued

| Comparative Experiment 1 | GHSV 336/hr | GHSV 600/hr |
|---|---|---|
| % Deep Oxidation | 37.46 | 22.58 |
| Furan/Benzene | 9.08 | 5.96 |
| Unknown | 0.00 | 3.43 |
| % Total Heavies | 9.08 | 9.39 |
| % Yield C4's | 34.25 | 34.60 |
| Total C balance | 101.9 | 98.19 |

*Catalyst, 15 cc; T = 550° C.

When Comparative Experiment 1 (GHSV 336 hr$^{-1}$) is compared with Examples 1-5, it is seen that the presence of cesium in the catalyst significantly improves the selectivities to butadiene and butenes. Simultaneously, the selectivities to undesirable heavies, such as furan and benzene, and especially deep oxidation products, such as carbon oxides, decrease. However, when Comparative Experiment 1 (GHSV 336 hr$^{-1}$) is compared with Examples 1-5, it is seen that the presence of cesium in the catalyst leads to a decrease in the butane conversion.

EXAMPLES 6-10

(a) Preparation of Alkali-Promoted Catalysts 6-10

A series of alkali-doped magnesium molybdate catalysts is prepared according to the following general procedure, with the exception that the amount of alkali metal hydroxide per 40 g methanolic solution is varied as follows: Catalyst 6, KOH, 0.049 g; Catalyst 7, KOH, 0.098 g; Catalyst 8, KOH, 0.133 g; Catalyst 9, KOH, 0.320 g; and Catalyst 10, NaOH, 0.073 g.

Ammonium heptamolybdate, (NH$_4$)$_6$Mo$_7$O$_{24}$·4H$_2$O (72 g; 0.0583 mole), is dissolved in 345 ml of water and the resulting solution is added to magnesia (300 g; CE Basic Industries, Magox Premium magnesia) to form a slurry. The slurry is dried at 70° C. for 18 hours and at 130° C. for 2 hours to obtain a solid mixture. The mixture is crushed and passed through a sieve to obtain particles having a 20-120 mesh size. The sieved particles are calcined by heating slowly over 5 hours to a temperature of 600° C. and then holding at 600° C. for 2 hours. The calcined solid is cooled to room temperature to yield magnesium molybdate containing 22 weight percent MoO$_3$ and 78 weight percent MgO. A methanolic solution is prepared by adding the appropriate weight of alkali metal hydroxide, noted hereinabove, to 40 g of methanolic solution. The magnesium molybdate solid is immersed for 15 minutes in the methanolic solution. The resulting mixture is filtered, dried in air for 4 hours at room temperature, and then dried in an oven at 120° C. for 16 hours. The dried solid is calcined by heating slowly over 5 hours to a temperature of 600° C. and then holding at 600° C. for 2 hours to yield an alkali-promoted magnesium molybdate catalyst. The weight percentage of alkali metal in Catalysts 6-10 is found in Table III.

TABLE III*

| Example | 6 | 7 | 8 | 9 | 10 |
|---|---|---|---|---|---|
| Catalyst | 6 (K$^+$) | 7 (K$^+$) | 8 (K$^+$) | 9 (K$^+$) | 10 (Na$^+$) |
| Weight % Alkali | 0.15 | 0.28 | 0.38 | 0.85 | 0.22 |
| Surface Area (m²/g) | 94.60 | 99.20 | 91.59 | 74.1 | 92.60 |
| % Conversion | 63.78 | 50.52 | 42.07 | 21.0 | 53.25 |
| Selectivities: | | | | | |
| 1-butene | 1.93 | 4.39 | 6.63 | 14.91 | 3.38 |
| trans-2-butene | 1.36 | 1.65 | 2.12 | 5.29 | 1.84 |
| cis-2-butene | 1.78 | 2.32 | 3.25 | 7.87 | 2.14 |

TABLE III*-continued

| Example | 6 | 7 | 8 | 9 | 10 |
|---|---|---|---|---|---|
| butadiene | 68.24 | 72.27 | 73.71 | 47.44 | 76.21 |
| % Total C4's | 73.31 | 80.63 | 85.71 | 75.51 | 83.57 |
| propylene | 0.31 | 0.53 | 0.88 | 4.06 | 0.39 |
| ethylene | 2.21 | 3.02 | 4.08 | 6.24 | 2.29 |
| % Total Cracking | 2.52 | 3.55 | 4.97 | 10.30 | 2.68 |
| $CO_2$ | 10.99 | 5.28 | 4.38 | 4.46 | 7.08 |
| CO | 4.39 | 1.89 | 2.73 | 1.09 | 3.03 |
| % Deep Oxidation | 15.39 | 7.17 | 7.10 | 5.55 | 10.11 |
| Furan/Benzene | 7.26 | 1.56 | 2.22 | 1.38 | 3.64 |
| Unknown | 1.52 | 7.08 | 0.00 | 7.27 | 0.00 |
| % Total Heavies | 8.79 | 8.64 | 2.22 | 8.65 | 3.64 |
| % Yield C4's | 46.76 | 40.73 | 36.06 | 15.86 | 44.50 |
| Total C balance | 99.03 | 96.42 | 100.58 | 98.48 | 101.82 |

*Catalyst, 15 cc; T = 550° C.; GHSV = 336 $hr^{-1}$.

(b) Oxidation of Butane Employing Catalysts 6–10

The potassium- and sodium-doped Catalysts 6–10, prepared hereinbefore, are employed in the oxidation of butane according to the procedure of Examples 1–5 (b). The results are set forth in Table III.

The data show that butane is oxidized predominantly to butadiene and butenes in the presence of the magnesium molybdate catalyst doped with potassium and sodium ions. Moreover, when Examples 6–10 are compared with Comparative Experiment 1 (GHSV, 336 $hr^{-1}$), it is seen that the catalysts doped with potassium or sodium ions (Catalysts 6–10) achieve significantly higher selectivities to butadiene and butenes than the undoped magnesium molybdate material. Simultaneously, the selectivity to deep oxidation products is significantly reduced in the alkali-doped catalysts.

EXAMPLES 11 AND 12

(a) Preparation of Potassium-Promoted Catalysts 11 and 12

Two solutions are prepared comprising ammonium heptamolybdate, $(NH_4)_6Mo_7O_{24}.4H_2O$ (35 g), and potassium carbonate in 125 g of aqueous solution. The first solution contains 0.63 g (Catalyst 11) of potassium carbonate, whereas the second solution contains 1.44 g (Catalyst 12) of potassium carbonate. Each solution is added to magnesia (100 g; CE Basic Industries, Magox Premium Grade magnesia) with stirring, and the resulting mixtures are dried and calcined as in the preparation of Catalysts 1–5 hereinbefore to yield potassium-doped magnesium molybdate catalysts.

(b) Oxidation of Butane Employing Catalysts 11 and 12

Catalysts 11 and 12 are employed in the oxidation of butane (Examples 11 and 12, respectively) according to the procedure of Examples 1–5. The results at a variety of process conditions are set forth in Table IV.

TABLE IV

| Example | 11 (a) | 11 (b) | 11 (c) | 12 (a) | 12 (b) | 12 (c) |
|---|---|---|---|---|---|---|
| Wt % K | 0.33 | 0.33 | 0.33 | 0.62 | 0.62 | 0.62 |
| Surface Area ($m^2/g$) | 116.0 | 116.0 | 116.0 | 124.0 | 124.0 | 124.0 |
| GHSV ($hr^{-1}$) | 600 | 600 | 336 | 600 | 600 | 336 |
| Temp. (°C.) | 550 | 570 | 550 | 550 | 570 | 550 |
| % Conversion | 59.93 | 70.58 | 75.12 | 46.22 | 57.25 | 58.47 |
| % Selectivity | | | | | | |
| 1-butene | 2.46 | 1.75 | 1.02 | 5.55 | 3.73 | 4.12 |
| tr-2-butene | 1.56 | 0.96 | 0.76 | 2.19 | 1.50 | 1.31 |
| cis-2-butene | 2.06 | 1.17 | 0.77 | 2.83 | 1.86 | 2.07 |
| butadiene | 71.58 | 68.53 | 62.43 | 75.38 | 74.16 | 73.48 |
| % Total C4's | 77.66 | 72.41 | 64.99 | 85.96 | 81.25 | 80.98 |
| propylene | 0.00 | 0.15 | 0.00 | 0.00 | 0.00 | 0.00 |
| ethylene | 1.76 | 2.99 | 2.03 | 2.39 | 2.91 | 3.77 |
| methane | 0.00 | 0.00 | 0.00 | 0.00 | 0.00 | 0.00 |
| % Total Cracking | 1.76 | 3.14 | 2.03 | 2.39 | 2.91 | 3.77 |
| $CO_2$ | 8.28 | 9.74 | 14.11 | 3.72 | 4.94 | 4.94 |
| CO | 3.28 | 4.71 | 6.33 | 1.75 | 2.11 | 2.80 |
| % Deep Oxidation | 11.65 | 14.45 | 20.44 | 5.47 | 7.05 | 7.74 |
| Furan/Benzene | 5.07 | 5.52 | 6.05 | 1.33 | 0.05 | 1.92 |
| Unknown | 3.85 | 4.48 | 6.49 | 4.85 | 8.73 | 5.58 |
| % Total Heavies | 8.93 | 10.00 | 12.54 | 6.18 | 8.79 | 7.51 |
| Total C Balance | 97.69 | 96.84 | 95.13 | 97.76 | 95.00 | 96.74 |

The data show that butane is oxidized predominantly to butenes and butadiene in the presence of a magnesium molybdate catalyst doped with potassium carbonate. The data show further that as the reaction temperature increases from 550° C. to 570° C., the butane conversion increases, while the selectivities to butenes and butadiene decrease. It is further observed that as the gas hourly space velocity decreases from 600 $hr^{-1}$ to 336 $hr^{-1}$, the butane conversion increases, while the selectivities to butenes and butadienes decrease. When Example 11 is compared with Example 12, it is seen that the catalyst containing the higher weight percentage of potassium gives a lower conversion of butane and a higher selectivity to butenes and butadienes. When Examples 12(a) and 12(c) are compared with Comparative Experiment 1(b) and 1(a), it is observed that the catalyst containing potassium ions gives significantly higher selectivities to butadiene, and lower selectivities to heavies and deep oxidation products than the comparative material with no alkali ions.

EXAMPLE 13

(a) Preparation of Potassium-Doped Catalyst 13

Ammonium vanadate, $NH_4VO_3$ (2.55 g; 0.022 mole), is added to 100 ml of water and the mixture is heated to 60° C. to promote dissolution. The temperature of the solution is raised to about 97° C. and ammonium heptamolybdate $(NH_4)_6Mo_7O_{24}.H_2O$ (18.5 g; 0.015 mole) is added with stirring. The resulting solution is boiled until the volume is reduced to 70 ml, whereupon magnesia (34 g; 0.85 mole) is added to yield a thick paste. An additional 50 ml of water is added to the thick paste to give a smooth creamy mixture. The cream is poured into a quartz crucible, air dried overnight, dried at 110° C. for two hours and calcined at 600° C. for two more hours to yield a calcined solid containing 4 weight percent $V_2O_5$, 30 weight percent $MoO_3$, and 65 weight percent MgO. Next, 8.2 ml of a methanolic solution containing potassium hydroxide (1 g KOH/100 ml solution) is diluted to a total of 16 ml volume with additional methanol. The diluted solution is added dropwise to the calcined solid (7.8 g), prepared hereinabove. The potassium hydroxide-impregnated solid is air dried for 30 minutes, then oven dried at 100° C. for one hour. The resulting solid comprises vanadium oxide, magnesium oxide, molybdenum oxide and about 1 weight percent potassium calculated as the hydroxide.

(b) Oxidation of Butane Employing Catalyst 13

Catalyst 13, prepared hereinabove, is employed in the oxidation of butane according to the procedure described in Examples 1–5 hereinbefore. The results are set forth in Table V.

TABLE V*

| Example | CE 2 | 13 |
|---|---|---|
| Weight % Alkali | 0 | 1 |
| % Conversion | 50 | 50 |
| % Selectivities: | | |
| butenes | 9.1 | 15.3 |
| butadiene | 51.1 | 58.2 |
| % Total C4's | 60.3 | 73.5 |
| $CO + CO_2$ | 32.7 | 16.9 |
| g $C_4$/g cat hr | 0.15 | 0.15 |

*Feedstream contains 20 vol. percent butane and 80 vol. percent nitrogen; T = 540° C.; Flow = 125 ml/min; 20 cycles.

It is observed that butane is oxidized predominantly to butadiene and butenes in the presence of a catalyst containing magnesium molybdate, vanadium oxide and potassium ions.

COMPARATIVE EXPERIMENT 2 (CE 2)

A comparative material is prepared as in Example 13 hereinabove, with the exception that the catalyst is not impregnated with potassium hydroxide. The comparative material contains 4 weight percent $V_2O_5$, 30 weight percent $MoO_3$, and 66 weight percent MgO. The comparative material is employed in the oxidation of butane according to the procedure described in Examples 1–5 hereinbefore. The results are set forth in Table V. When Comparative Experiment 2 is compared with Example 13, it is seen that the presence of potassium promoter in the catalyst significantly increases the selectivities for butadiene and butenes, and decreases the selectivity for deep oxidation products.

EXAMPLE 14

(a) Preparation of Potassium-Promoted Catalyst 14

Ammonium heptamolybdate, $(NH_4)_6Mo_7O_{24}\cdot 4H_2O$ (13.5 g; 0.011 moles), is dissolved in 120 ml of water, and the resulting mixture is heated to 60° C. to make a solution. Magnesium oxide (39 g) is added to the solution gradually over a period of 5 minutes and with vigorous stirring to make a smooth slurry. The slurry is dried at 110° C. overnight to obtain a cake, which is calcined in air at 600° C. for two hours to yield a magnesium oxide-molybdenum oxide mixture. The powdery oxide mixture is densified by pressing with 20,000 pounds force in a Carver press to yield a 1⅛-inch pellet. The pellet is broken into several pieces and impregnated with a methanolic solution of potassium hydroxide containing 1 g KOH per 100 ml methanol. A loading of 0.5 weight percent potassium hydroxide is achieved. The potassium hydroxide-impregnated magnesium molybdate catalyst is air dried for 2 hours, then dried in an oven at 110° C. for 2 additional hours.

(b) Oxidation of Butane Employing Catalyst 14

The potassium hydroxide-impregnated magnesium molybdate catalyst (Catalyst 14, 7.15 g), prepared hereinabove, is loaded into the tubular reactor operating in the pulse mode as in Examples 1–5, described hereinbefore. Butane is oxidized under reaction conditions and with the results set forth in Table VI.

TABLE VI

| T °C. | % Butane in feed × 0.01 | GHSV $hr^{-1}$ | % Butane Conv. × 0.01 | % $C4^1$ Sel. × 0.01 | % $BD^2$ Sel. × 0.01 | Sum $C4^1$ $STY^3$ | BD $STY^3$ |
|---|---|---|---|---|---|---|---|
| 540 | 0.10 | 750 | 0.37 | 0.81 | 0.67 | 22 | 18 |
| 540 | 0.20 | 750 | 0.34 | 0.88 | 0.71 | 45 | 36 |
| 540 | 0.30 | 750 | 0.33 | 0.91 | 0.74 | 68 | 55 |
| 560 | 0.30 | 750 | 0.49 | 0.80 | 0.72 | 88 | 79 |
| 560 | 0.40 | 750 | 0.44 | 0.82 | 0.71 | 109 | 93 |
| 560 | 0.50 | 750 | 0.42 | 0.81 | 0.69 | 128 | 108 |
| 560 | 0.30 | 1200 | 0.31 | 0.90 | 0.71 | 100 | 79 |
| 580 | 0.50 | 750 | 0.53 | 0.74 | 0.65 | 147 | 129 |
| 580 | 0.70 | 750 | 0.46 | 0.74 | 0.63 | 179 | 152 |
| 580 | 0.50 | 1200 | 0.41 | 0.82 | 0.68 | 202 | 167 |
| 580 | 0.90 | 1200 | 0.33 | 0.79 | 0.59 | 284 | 212 |

[1]C4 refers to butadienes and butenes.
[2]BD refers to butadiene.
[3]STY refers to space time yield, in units of mole percent $hr^{-1}$.

The data show that butane is oxidized in the presence of a potassium-doped magnesium molybdate catalyst to butadiene and butenes, predominantly. Moreover, it is observed that at constant temperature and gas hourly space velocity, the butadiene space-time yield increases significantly with increasing percentage of butane in the feed. Under the same conditions, the conversion of butane and the selectivity to butadiene is maintained at a high level. The same observations are made for the sum of the $C_4$ (butadiene and butenes) space-time yield and selectivity.

What is claimed is:

1. A process of preparing an unsaturated aliphatic hydrocarbon comprising contacting an aliphatic hydrocarbon having at least three carbon atoms with a solid heterogeneous catalyst having labile oxygen under conditions such that an unsaturated aliphatic hydrocarbon is produced in a selectivity of at least about 50 mole percent, the catalyst consisting essentially of an oxide of magnesium, an oxide of molybdenum and a Group IA alkali metal promoter in a concentration from about 0.1 weight percent to about 5 weight percent calculated as the alkali hydroxide and based on the combined weight of the magnesium and molybdenum oxides.

2. The process of claim 1 wherein the aliphatic hydrocarbon is an alkane represented by the general formula:

$$CH_3-(CH_2)_n-CH_3$$

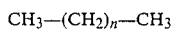

wherein n is an integer from 1 to about 8.

3. The process of claim 2 wherein n is 2 and the alkane is n-butane.

4. The process of claim 1 wherein the aliphatic hydrocarbon is diluted with a non-reactive gas in a hydrocarbon concentration ranging from about 10 mole percent to about 90 mole percent.

5. The process of claim 4 wherein the hydrocarbon concentration ranges from about 40 mole percent to about 90 mole percent.

6. The process of claim 1 wherein the oxide of magnesium and the oxide of molybdenum are combined to form magnesium molybdate.

7. The process of claim 1 wherein the temperature is in the range from about 400° C. to about 700° C.

8. The process of claim 1 wherein the aliphatic hydrocarbon partial pressure is in the range from about atmospheric to about 100 psia.

9. The process of claim 1 wherein the gas hourly space velocity of the feedstream is in the range from about 100 hr$^{-1}$ to about 10,000 hr$^{-1}$.

10. The process of claim 1 wherein the unsaturated aliphatic hydrocarbon is a diolefin and wherein the diolefin is represented by the general formula:

$$CH_2=CH-CH=CH-(CH_2)_m-H$$

wherein m is an integer from 0 to about 6.

11. The process of claim 10 wherein m is 0 and the diolefin is 1,3-butadiene.

12. The process of claim 1 wherein the amount of alkali metal promoter is in the range from about 0.2 weight percent promoter to about 2 weight percent promoter.

13. A process of preparing 1,3-butadiene comprising contacting n-butane with a solid heterogeneous catalyst containing labile oxygen at a temperature in the range from about 500° C. to about 650° C., and a pressure in the range from about 1.5 psia to about 30 psia, and a gas hourly space velocity in the range from about 400 hr$^{-1}$ to about 4,000 hr$^{-1}$, and under such other reaction conditions that a mixture of products is formed containing 1,3-butadiene in a selectivity of at least about 50 mole percent, said catalyst consisting essentially of a magnesium oxide, a molybdenum oxide and a Group IA alkali metal promoter in a concentration from about 0.1 weight percent to about 5 weight percent calculated as the alkali hydroxide and based on the weight of the magnesium-molybdenum oxides.

14. The process of claim 13 wherein the selectivity to butadiene is at least about 70 mole percent.

15. The process of claim 13 wherein the space-time yield of butadiene is at least about 200 mole percent hr$^{-1}$.

16. A process of preparing an unsaturated aliphatic hydrocarbon comprising contacting an aliphatic hydrocarbon having at least three carbon atoms with a solid heterogeneous catalyst having labile oxygen under conditions such that an unsaturated aliphatic hydrocarbon is produced in a selectivity of at least about 50 mole percent, the catalyst consisting essentially of an oxide of magnesium, an oxide of molybdenum, and a Group IA alkali metal promoter selected from the group consisting of an alkali metal oxide, hydroxide, carbonate, acetate and oxalate, the promoter being in a concentration from about 0.1 weight percent to about 5 weight percent calculated as the alkali hydroxide and based on the combined weight of the magnesium and molybdenum oxides.

17. The process of claimed 13 of preparing 1,3-butadiene comprising contacting n-butane with a solid heterogeneous catalyst containing labile oxygen at a temperature in the range from about 500° C. to about 650° C., and a pressure in the range from about 1.5 psia to about 30 psia, and a gas hourly space velocity in the range from about 400 hr$^{-1}$ to about 4,000 hr$^{-1}$, and under such other reaction conditions that a mixture of products is formed containing 1,3-butadiene in a selectivity of at least about 60 mole percent, said catalyst consisting essentially of a magnesium oxide, a molybdenum oxide, and a Group IA alkali metal promoter in a concentration from about 0.1 weight percent to about 5 weight percent calculated as the alkali hydroxide and based on the weight of the magnesium-molybdenum oxides.

18. The process of claim 13 of preparing 1,3-butadiene comprising contacting n-butane with a solid heterogeneous catalyst containing labile oxygen at a temperature in the range from about 500° C. to about 650° C., and a pressure in the range from about 1.5 psia to about 30 psia, and a gas hourly space velocity in the range from about 400 hr$^{-1}$ to about 4,000 hr$^{-1}$, and under such other reaction conditions that a mixture of products is formed containing 1,3-butadiene in a selectivity of at least about 50 mole percent and wherein the space-time yield of butadiene is at least about 120 mole percent hr$^{-1}$, said catalyst consisting essentially of a magnesium oxide, a molybdenum oxide, a Group IA alkali metal promoter in a concentration from about 0.1 weight percent to about 5 weight percent calculated as the alkali hydroxide and based on the weight of the magnesium-molybdenum oxides.

19. The process of claim 16 wherein the alkali metal is cesium.

20. The process of claim 16 wherein the alkali metal is potassium.

21. The process of claim 16 wherein the sum of the selectivities to C$_4$ alkenes is at least about 80 mole percent.

22. A solid heterogeneous catalyst composition consisting essentially of an oxide of magnesium, an oxide of molybdenum, and a Group IA alkali metal promoter in a concentration from about 0.1 weight percent to about 5 weight percent calculated as alkali hydroxide and based on the weight of the combined magnesium and molybdenum oxides, said composition being capable of providing a labile form of oxygen.

23. The catalyst of claim 22 wherein the molybdenum oxide concentration ranges from about 6 weight percent MoO$_3$ to about 50 weight percent MoO$_3$ based on the weight of the combined magnesium and molybdenum oxides.

24. The catalyst of claim 22 wherein the molybdenum oxide concentration ranges from about 10 weight percent MoO$_3$ to about 30 weight percent MoO$_3$ based on the weight of the combined magnesium and molybdenum oxides.

25. The catalyst of claim 22 wherein the magnesium oxide concentration ranges from about 94 weight percent MgO to about 50 weight percent MgO based on the weight of the combined magnesium and molybdenum oxides.

26. The catalyst of claim 22 wherein the alkali metal promoter concentration ranges from about 0.2 weight percent to about 2 weight percent.

27. The catalyst of claim 26 wherein the alkali metal promoter concentration ranges from about 0.5 weight percent to about 1.5 weight percent.

28. The catalyst of claim 22 wherein the alkali metal promoter is an alkali metal oxide, hydroxide, carbonate, acetate, or oxalate.

29. The catalyst of claim 28 wherein the alkali metal promoter is an oxide or hydroxide of potassium or cesium.

30. A process of preparing 1,3-butadiene comprising contacting n-butane with a solid heterogeneous catalyst containing labile oxygen at a temperature in the range from about 500° C. to about 650° C., and a pressure in the range from about 1.5 psia to about 30 psia, and a gas hourly space velocity in the range from about 400 hr$^{-1}$ to about 4,000 hr$^{-1}$, and under such other reaction conditions that a mixture of products is formed containing 1,3-butadiene in a selectivity of at least about 50 mole percent and wherein the sum of the selectivities to C$_4$ alkenes is at least about 60 mole percent, said catalyst consisting essentially of a magnesium oxide, a molybdenum oxide, a vanadium oxide, and a Group IA alkali metal promoter in a concentration from about 0.1 weight percent to about 5 weight percent calculated as the alkali hydroxide and based on the weight of the magnesium-molybdenum oxides.

31. A solid heterogeneous catalyst composition consisting essentially of an oxide of magnesium, an oxide of molybdenum, and an oxide or hydroxide of potassium in a concentration from about 0.1 weight percent to about 5 weight percent calculated as potassium hydroxide and based on the weight of the combined magnesium and molybdenum oxides, said composition being capable of providing a labile form of oxygen.

32. A process of preparing a solid heterogeneous catalyst composition consisting essentially of an oxide of magnesium, an oxide of molybdenum, and a Group IA alkali metal promoter in a concentration from about 0.1 weight percent to about 5 weight percent calculated as alkali hydroxide and based on the weight of the combined magnesium and molybdenum oxides, said composition being capable of providing a labile form of oxygen, the process comprising (a) preparing a solution of an oxide of molybdenum or a precursor thereof, (b) pouring said solution over magnesium oxide to form a slurry, (c) calcining said slurry at a temperature sufficient to form a magnesium oxide and molybdenum oxide mixture having a composition in the range from about 6 weight percent to about 50 weight percent MoO$_3$, and from about 94 weight percent to about 50 weight percent MgO, and (d) impregnating said oxide mixture with a solution of a Group IA alkali metal promoter such that the concentration of alkali is in the range from about 0.1 weight percent to about 5 weight percent calculated as the alkali metal hydroxide and based on the weight of the magnesium-molybdenum oxide mixture.

33. A process of preparing an unsaturated aliphatic hydrocarbon comprising contacting an aliphatic hydrocarbon having at least three carbon atoms with a solid heterogeneous catalyst having labile oxygen under conditions such that an unsaturated aliphatic hydrocarbon is produced in a selectivity of at least about 50 mole percent, the catalyst consisting essentially of an oxide of magnesium, an oxide of molybdenum, an oxide of vanadium, and a Group IA alkali metal promoter in a concentration from about 0.1 weight percent to about 5 weight percent calculated as the alkali hydroxide and based on the combined weight of the magnesium and molybdenum oxides.

34. A solid heterogeneous catalyst composition consisting essentially of an oxide of magnesium, an oxide of molybdenum, an oxide of vanadium, and a Group IA alkali metal promoter in a concentration from about 0.1 weight percent to about 5 weight percent calculated as alkali hydroxide and based on the weight of the combined magnesium and molybdenum oxides, said composition being capable of providing a labile form of oxygen.

* * * * *